United States Patent [19]

Redikultsev et al.

[11] Patent Number: 4,656,138
[45] Date of Patent: Apr. 7, 1987

[54] FERMENTER

[75] Inventors: Jury V. Redikultsev; Leonid A. Litvinenko; Taisia S. Chermenskaya; Svetlana B. Petrikevich; Mikhail G. Maximov, all of Moskovskaya, U.S.S.R.

[73] Assignee: Institut Biokhimii I Fiziologii Mikroorganizomov, Moskovskoi, U.S.S.R.

[21] Appl. No.: 618,679

[22] PCT Filed: Apr. 29, 1983

[86] PCT No.: PCT/SU83/00009
§ 371 Date: Jun. 4, 1984
§ 102(e) Date: Jun. 4, 1984

[87] PCT Pub. No.: WO84/01582
PCT Pub. Date: Apr. 26, 1984

[30] Foreign Application Priority Data

Oct. 10, 1982 [SU] U.S.S.R. .............................. 3494601

[51] Int. Cl.$^4$ .............................................. C12M 1/06
[52] U.S. Cl. ...................................... 435/314; 435/315
[58] Field of Search ............... 435/315, 314, 316, 305; 261/119 R, 36 R; 417/383

[56] References Cited

U.S. PATENT DOCUMENTS

| 2,146,326 | 2/1939 | Bergius | 435/316 X |
| 3,664,770 | 5/1972 | Palmer | 417/383 |
| 3,713,988 | 1/1973 | Dawson | 435/316 X |
| 3,824,151 | 7/1974 | Iijima | 435/315 X |
| 4,173,516 | 11/1979 | Katinger | 435/286 |
| 4,255,360 | 3/1981 | Jeffries | 261/119 R |

FOREIGN PATENT DOCUMENTS 1151526 8/1978 United Kingdom .
373292 3/1971 U.S.S.R. .

Primary Examiner—Alan Cohan
Attorney, Agent, or Firm—Lilling & Greenspan

[57] ABSTRACT

The invention relates to apparatus for cultivating microbiological substances. The fermenter comprises a container (1) accommodating an aerator (4) and a stirring unit (5) having the form of a circulation tube (6) and membrane (7). A partition (9) having a through hole (10) offset relative to the center thereof is disposed between the membrane (7) and the end of the tube (6) to define with the membrane (7) a closed volume (11). The aerator (4) and the stirring unit (5) are integrated into a single assembly secured on the partition (9) and having a chamber (12) for distributing liquid and gas flows. The fermenter is intended for intermittent cultivation of various substances of biological origin feeding on liquid, solid or mixed nutrient substrates.

4 Claims, 5 Drawing Figures

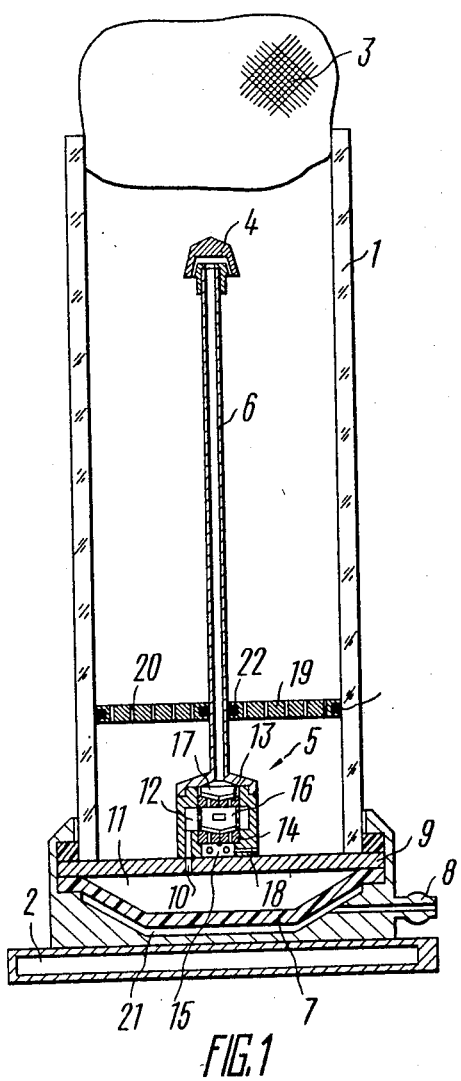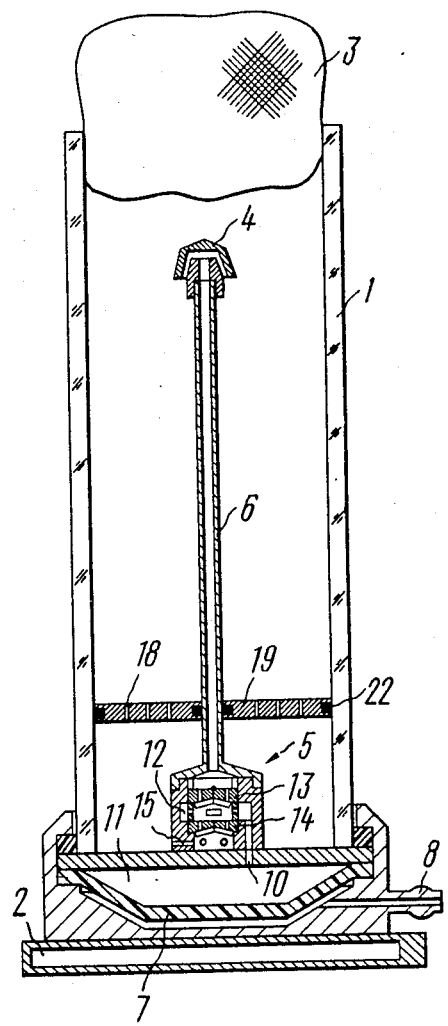

FERMENTER

BACKGROUND OF THE INVENTION

1. Field of the Invention

This invention relates to apparatus for periodic cultication of various microbodies of biological origin fed on solid, liquid or combination nutrient substrates, and more particularly to fermenters.

2. Description of Related Art

Any fermentation process involves a complex of interconnected biochemical, physicochemical and diffusive transformations dependent in their intensity mostly on the conditions of operation of the fermenter and its hydrodynamic characteristics.

For cultivating microorganisms, fungi, algae or separate tissues the microbiological practice has widely used flasks stopped by cotton filters and accommodating microbodies to be grown in a temperature-controlled rocker. Such devices are sufficiently simple and allow the growth of a range of various microbodies. However, despite their multipurpose application, their use is inherently confined in laboratory practice due to insufficient mass transfer. In addition, the flasks are not adaptable for cultivating microbodies of biological origin fed on solid nutritive substrates.

There are known different structural arrangements of fermenters; each such arrangement posessing hydrodynamic characteristics providing for the active growth of this or that type of microbody.

In particular, there is known a fermenter comprising a container with a stirring unit in the form of a multistage mixer (cf., e.g., E. U. Viestur, et al "Kultivirovanie mikroorganizmov"—Cultivation of Microorganisms, in Russian, Moscow, 1980, pp. 141 to 171).

This fermenter can be used for growing bacteria of yeast on a liquid nutritive medium and is not adapted for operation on solid or combination-type substrates.

The stirring units used in these fermenters tend to produce excessive foam in the cultural liquid, whereas for damping or supressing the foam use is made of mechanical, chemical or combined foam suppression, which affects the process parameters. In addition, the above apparatus provide only for cultivation of one or two types of microorganisms, such as yeast or bacteria.

There is also known a fermenter comprising a container provided with a heat-transfer jacket, a bacterial filter disposed in its inlet, an aerator, and a stirring unit in the form of a vertical circulation tube having a membrane accommodated under its lower end and connected with a drive (cf., a pamphlet of the Bioengineering AG Company, Switzerland).

The fermenter of its construction is adapted for use with bacteria or yeast fed on liquid nutritive substrates. The saturation of the cultural liquid with the oxygen of the air and mixing thereof in such a fermenter is assured by sucking in the air through the aerator to the vertical circulation tube accompanied by the formation therein of a gas-liquid mixture.

This fermenter is not capable of growing fungi, algae and separate tissue, and is not adapted for carrying out the processes of microbiological transformation of biologically active substances by using immobilized cells; it is also not adapted to operate on solid or combination substrates.

This is accounted for by the fact that aeration in said fermenter takes place by virtue of suction of air by a jet of liquid with the escape velocity thereof depending on its viscosity. Thus, during cultivation of mycelium the speed of flow of the cultural liquid is sharply reduced, and aeration terminates completely.

The free access of the substrate to the membrane prevents the fermentation process using solid or combination substrates, because such insoluble substrates (e.g., straw, wood saw dust, coal, etc.) tend to block the inlet of the circulation tube to result in plugging thereof and termination of the fermentation process.

For similar reasons the use of the above fermenter for carrying out processes involving a separate tissue or immobilized cells is impossible.

SUMMARY OF THE INVENTION

The invention is directed toward the provision of a fermenter having a construction as to expand its functional capabilities and make it applicable for growing microorganisms, algae or separate tissues on solid, liquid or combination substrates.

The aim of the invention is attained by a fermenter comprising a container with an inlet having secured therein a bacterial air filter and provided with a heat-transfer jacket. The container accommodates therein an aerator and a stirring unit in the form of a vertical circulation tube and a membrane underlying its lower end and connected to a control drive. According to the invention, a rigid partition wall is disposed between the membrane and the lower end of the circulation tube, this rigid partition wall being provided with a through hole off-set relative to the center thereof and defining with the membrane a closed volume, whereas the aerator and the stirring unit are made in the form of an integrated assembly secured on the partition wall and having a chamber for distribution of liquid and gas flows and separated in terms of height by two non-return valves into three cavities of which one cavity lies between the valves and communicates with the hole made in the rigid partition wall, the other cavity underlies the valves and communicates with a liquid zone of the container, and the third cavity overlies the valves and communicates with the interior of the circulation tube the upper end of which is extended toward a gas zone of the container.

Preferably, a headpiece for forming a flow of liquid ejected from the tube is secured on the upper end of this tube.

Advisably, the container accommodates a horizontal platform having holes therein and serving to support a solid nutrient substrate.

The fermenter embodying the features of the present invention can be used for cultivating microorganisms, algae, or separate tissues on liquid, solid or combination substrates.

The use in the proposed fermenter of pulsewise stirring in combination with the structural peculiarities of the stirring unit made integral with the aerator provides in the fermenter jet or bubble mixing of the cultural liquid, which is especially advantageous for selecting proper hydrodynamic conditions for growing particular types of microorganisms.

The provision of the horizontal perforated platform and replaceable headpieces on the aerator makes it possible to grow a variety of aerobic microorganisms, mycelium, separate tissues, and photoautotrophic organisms on liquid, solid or combination substrates, as well as to carry out processes involving immobilized ferments or cells.

BRIEF DESCRIPTION OF THE DRAWINGS

The invention will now be described in greater detail with reference to various specific embodiments thereof taken in conjunction with the accompanying drawings, in which:

FIG. 1 is a longitudinal sectional view of the fermenter according to the invention;

FIG. 3 illustrates substantially the same as shown in FIG. 1; non-return valves for distributing liquid and gas flows being in an upside down position;

DESCRIPTION OF THE PREFERRED EMBODIMENTS

Figure 4:
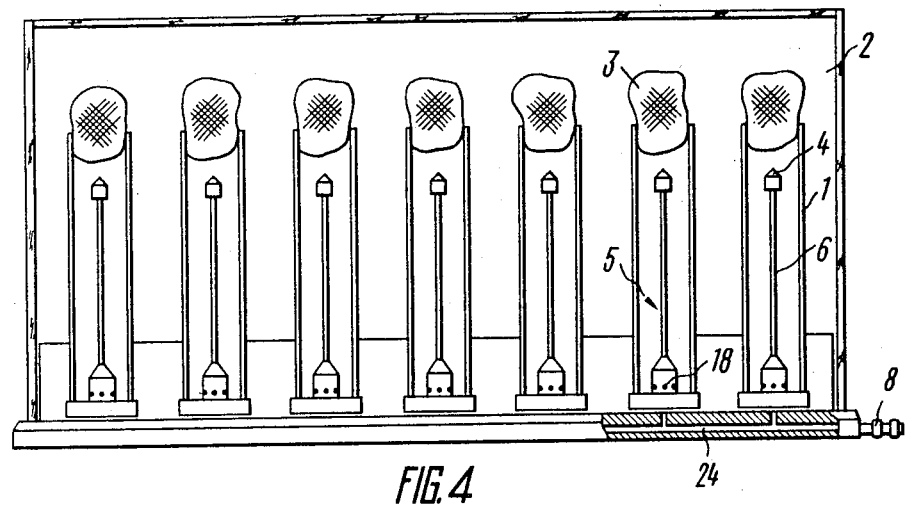
FIG. 4 is a modified form of the fermenter according to the invention comprised of seven containers and a common membrane movable from one drive.

A fermenter illustrated in FIG. 1 comprises a container 1 provided with a heat transfer jacket 2 and having a bacterial filter 3 disposed at an inlet of the container 1. The container 1 also accommodates an aerator 4 and a stirring unit 5 in the form of a vertical circulation tube 6 and a membrane 7 underlying its lower end and connected to a controlling pneumatic drive (not shown) by means of a pipe 8.

Interposed between the membrane 7 and the circulation tube 6 is a rigid partition wall 9 having a through hole 10 offset relative to the center of the partition wall 9 to form with the membrane 7 a closed volume 11. The aerator 4 and the stirring unit 5 are integrated into a single assembly secured on the partition wall 9 and having a chamber 12 for distributing liquid or gas flows. The chamber 12 is separated in terms of its height by two non-return valves 13 and 14 into three cavities 15, 16 and 17, of which the intervalve cavity 16 communicates with the hole 10 made in the rigid partition wall 9, the undervalve cavity 15 communicating through holes 18 with a liquid zone of the container 1, and the overvalve cavity 17 communicates with the interior of the circulation tube 6 the upper end of which is extended toward a gas zone of the container 1.

Secured on the upper end of the circulation tube 6 is a replaceable headpiece or aerator 4 in the embodiment described in the form of a jet injector.

The container 1 also accommodates a horizontal platform 19 having holes 20 and serving to support a solid nutrient substrate.

The fermenter shown in FIG. 1 is a multifunction inoculator-type fermenter intended for cultivation of microorganisms in laboratories, particularly for growing such living cells as bacteria, yeast and other anaerobic microorganisms fed on liquid or mixed nutrient substrates.

The fermenter operates in the following manner.

The container 1 is filled with a culture liquid with a level thereof not in excess of the level at which the jet injector (aerator 4) is disposed to be then stopped by the bacterial filter 3. Compressed air is supplied from a generator of pneumatic pulses (not shown) at a predetermined pulse frequency through the pipe 8 to a chamber 21 underlying the membrane 7.

The membrane 7 is caused to oscillate and during its downward travel acts to suck the cultural liquid through the holes 18, valve 14, cavity 15 and hole 10 into the closed volume 11; the non-return valve 13 being closed.

During the upward movement of the membrane 7 the cultural liquid occupying the volume 11 is forced therefrom through the hole 10, cavity 16, non-return valve 13, circulation tube 6 and aerator 4 (jet injector) in the form of jets back to the container 1; the non-return valve 14 being closed. The jets of cultural liquid formed in the injector (aerator 4) penetrate through the body of cultural liquid occupying the container 1 to disperse oxygen of the air therein entrained by the jets from the gas zone of the container 1.

During oscillations of the membrane 7 the level of the cultural liquid in the container 1 also tends to oscillate to follow the movements executed by the membrane 7 and thereby carry out the exchange of air occupying the gas zone of the container 1 with the atmospheric air through the bacterial filter 3.

In the case of using combination nutrient substrates, use is made of the horizontal perforated platform 19 secured on the circulation tube 6 and walls of the container 1 by means of elastic rings 22. When microorganisms are grown on such nutrient substrates, solid insoluble components of such nutrient media are retained on the platform 19 and fail to contaminate the stirring unit 5. The pulsewise operation of the membrane 7 and the oscillations of the entire body of the cultural liquid prevents obstruction of the holes 20 of the platform 19 by the insoluble solids contained in the substrate.

When the cultural liquid generates too much foam, the foam covers the injector or aerator 4 and the jets of the cultural liquid act to reduce the dispersion of air in the cultural liquid and thereby stabilize froth formation at this level.

In such conditions of operation of the fermenter mass transfer of the cultural liquid is effected through vigorous mixing and recirculation of the foam; such a mass transfer is no less efficient than during jet dispersion of the oxygen of the air in the cultural liquid.

Figure 2:
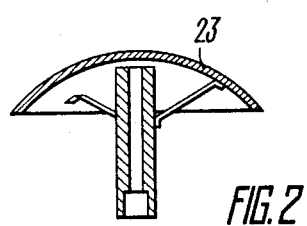
FIG. 2 is a longitudinal sectional view of a headpiece for forming a flow of liquid.

With reference to FIG. 2, there is shown one more embodiment of the headpiece-aerator in the form of a semisphere 23 acting to generate a substantially flat annular flow of liquid.

The use of the semisphere 23 instead of the jet injector represented in FIG. 1 allows production of a very thin film of cultural liquid flowing down on the transparent walls of the container 1 for the fermenter according to the invention to be capable of growing photoautotrophic microorganisms and algae.

A modified form of the fermenter according to the invention illustrated in FIG. 3 is different from the fermenter shown in FIG. 1 only in positioning of the valves 13 and 14. The valves 13 and 14 in the fermenter of FIG. 3 are turned upside down as compared to the modification of the fermenter represented in FIG. 1 to provide for pulsewise bubbling operation of the fermenter.

This modification is also a multifunctional inoculator-type fermenter intended for laboratory cultivation of aerobic microorganisms or fungus mycelium grown on solid, liquid or mixed substrates, as well as for carrying out the processes of transformation of steroids with immobilized cells or ferments, or for growing a separate living tissue.

The modified form of the fermenter shown in FIG. 2 operates in the following manner.

The container 1 is filled with a cultural liquid to a level not exceeding the level at which the aerator 4 is disposed, the container is then closed by the bacterial filter 3. Compressed air is fed from a generator of pneumatic pulses (not shown) at a predetermined pulse frequency through the pipe 8 to the chamber 21 under the membrane 7.

The membrane 7 is therefore caused to reciprocate or oscillate, and during an upward travel to force air from the closed volume 11 through the hole 10, cavity 16, valve 14 and holes 18 to the part of the container 1 occupied by the liquid, the thus forced air tending to cause bubbling and vigorous stirring of the body of cultivated liquid to saturate it with the oxygen of the air. The valve 13 is closed during this stirring action. During the reverse travel of the membrane 7 the valve 14 is closed, and the air is again passed to the closed volume 11 from the gas zone of the container 1 through the aerator 4, circulation tube 6, valve 13, cavity 16 and hole 10. Exchange of air occupying the gas zone of the container 1 with the atmospheric air is effected through the bacterial filter 3 synchronously with the movements of the membrane 7 similarly to what has been described with reference to the modification shown in FIG. 1.

In the case of excessive foaming of the cultural liquid, the foam tends to envelope the aerator 4 to be delivered instead of air to the closed volume 11, whereby aeration of the cultural liquid will be less vigorous and the level of foam in the container 1 will be stabilized.

Mass transfer in the fermenter in this case will take place due to a highly intensive circulation of the foam; this mass transfer being as efficient as when bubbling takes place in the fermenter.

When growing microorganisms on solid substrates or during carrying out the processes of transformation of steroid compounds with an immobilized biocatalyst, these compounds are placed on the horizontal platform 19 to be aerated by air fed in a pulsewise manner through the holes 20 in response to the movement of the membrane 7.

During growing fungus mycelium on such solid substrates as hay, the air conveyed for aeration can be moistened by accommodating in the space under the horizontal platform 19 a liquid nutrient medium or water. The mycelium growth process in this case is carried out similarly to what has been described with reference to bubbling aeration of the cultural liquid.

The fermenter shown in FIG. 4 is a multifunctional cultivator type intended for cultivation of aerobic microorganisms by using various nutrient substrates, separate tissue cultures, and photoautotrophic microorganisms and algae, as well as for carrying out the processes of transformation of biological compounds making use of immobilized ferments or cells.

This modified form of the proposed fermenter is a set of seven fermenters generally similar to the one described with reference to FIG. 1 and accommodated in a single heat transfer jacket 2. Cavities 21 of all of the fermenters are integrated into a single common cavity by a conduit 24 communicated by the pipe 8 with a controlling pneumatic drive (not shown).

This fermenter is intended predominantly for laboratory use. It can find a wide application in research and development, for microbiological and medicinal practice, as well as in sanitation control laboratories for checking the level of bacterial contamination of environments, etc. It can further be used in research practice for routine analytical and inspection operations where for these purposes bulky and energy-consuming flasks are used. The apparatus has a provision for a self-contained or independent temperature control, and has no need for temperature-adjusted rooms.

This modification of the fermenter is especially advantageous for selecting optimized dynamic conditions for growing a chosen microorganism.

The fermenter illustrated in FIG. 4 operates substantially in the same manner as those represented in FIGS. 1 and 3, although a feature which distinguishes it from the previously described modifications resides in the use of a common drive providing for a synchronous operation of all the seven fermenters in both equal and different stirring conditions therein. This provides for growing microorganisms simultaneously in seven reproductions, which is especially important for research practice.

Figure 5:
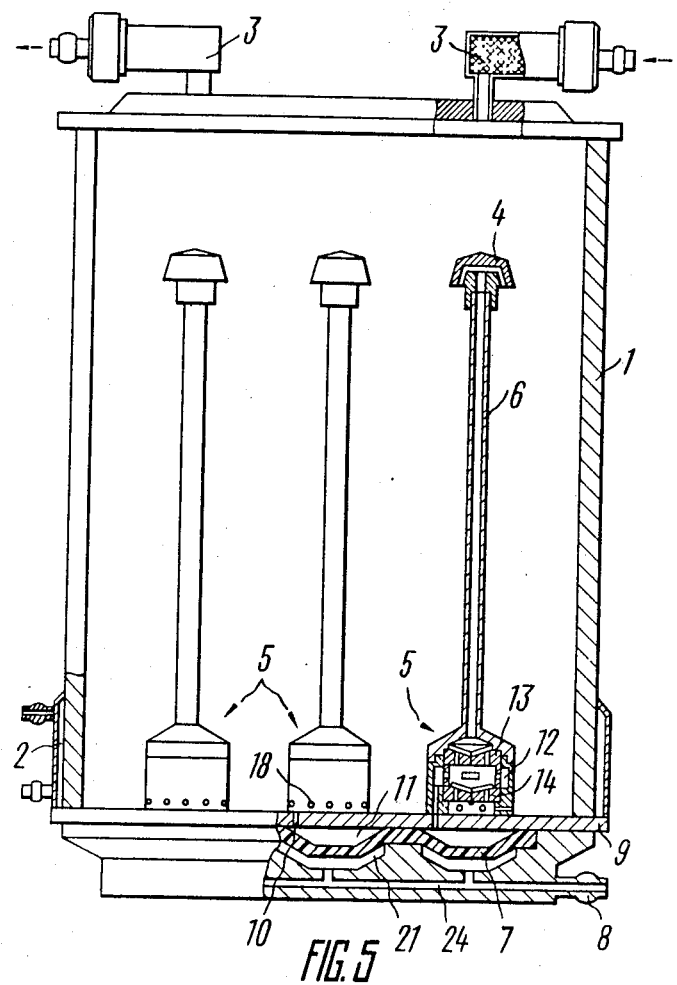
FIG. 5 is a modification of a multifunctional fermenter adapted for industrial application.

As distinct from the aforedescribed modified forms of the fermenters according to the invention, the fermenter shown in FIG. 5 comprises several, in the case described three, stirring units 5 in one container 1, these stirring units 5 being mounted on a partition wall indicated by the same numeral 9 and adaptable for different rates of aeration and stirring in a range of various ratios.

For example, one unit 5 intended for producing bubbles may be disposed in the central part of the container 1 with two of jet stream operated units 5 arranged at the periphery.

Therefore, the fermenter thus constructed can provide for combination conditions of stirring assuring counter-directed flows of gas and liquid promoting a more vigorous saturation of the cultural liquid with gas, which expands the functional capabilities of the fermenter, especially with a foamy substrate, when it is necessary to increase the rate of mass transfer thanks to more active circulation of the foam without resorting to an increase in its volume.

In addition, such an arrangement of the units 5 promotes additional removal from the walls of the container 1 of particles of the substrate of microorganisms tending to adhere thereto.

The fermenter operates from a single drive through the pipe 8 and conduit 24 communicable with the cavities 21 arranged under the membranes 7.

The fermenter embodying the present invention can perform a multitude of functions and can find application:

in the microbiological practice, as a fermenter for carrying out the processes of microbiological synthesis of protein products, bioconversion of vegetable materials, utilization of wastes, etc.;

in the food industry as a mixer or an apparatus for stirring liquid media, for conducting fermentation processes, etc.;

in the pharmaceutical industry, as a reactor for making medicinal preparations, such as during transformation of steroids, etc.; and in the chemical industry, as a reactor for mixing liquid media and carrying out the reactions involving the use of solid catalysts.

We claim:

1. A fermenter comprising a container with an inlet having secured therein a bacterial air filter and provided with a heat-transfer jacket, the container having accommodated therein an aerator and a stirring unit in the form of a vertical circulation tube and a membrane underlying its lower end and connected to a control drive, characterized in that a rigid partition wall (9) is disposed between the membrane (7) and the lower end of the circulation tube (6), this rigid partition wall (9)

being provided with a through hole (10) offset relative to the center thereof and defining with the membrane (7) a closed volume (11), the aerator (4) and the stirring unit (5) being made in the form of an integrated assembly secured on the partition wall (9) and having a chamber (12) for distribution of liquid and gas flows and separated in terms of height by two non-return valves (13, 14) into three cavities (15, 16, 17) of which the cavity (16) lying between the valves communicates with the hole (10) made in the rigid partition wall (9), the cavity (15) underlying the valves communicating with a liquid zone of the container (1), and the cavity (17) overlying the valves communicating with the interior of the circulation tube (6) the upper end of which is extended toward a gas zone of the container (1).

2. A fermenter as claimed in claim 1, characterized in that a headpiece (aerator 4) for forming a flow of liquid ejected from the tube (6) is secured on the upper end of this tube (6).

3. A fermenter as claimed in claim 1, characterized in that the container (1) accommodates a horizontal platform (19) having holes (20) and serving to support a solid nutrient substrate.

4. A fermenter as claimed in claim 2, characterized in that the container (1) accommodates a horizontal platform (19) having holes (20) and serving to support a solid nutrient substrate.

* * * * *